(12) United States Patent
Olsson et al.

(10) Patent No.: US 11,723,583 B2
(45) Date of Patent: Aug. 15, 2023

(54) DEVICE AND A METHOD FOR DETECTION OF CHANGES IN TISSUE

(71) Applicant: Skindicator AB, Malmo (SE)

(72) Inventors: Lennart Olsson, Malmo (SE); Sven Van Dijkman, Skanor (SE)

(73) Assignee: SKINDICATOR AB

( * ) Notice: Subject to any disclaimer, the term of this patent is extended or adjusted under 35 U.S.C. 154(b) by 309 days.

(21) Appl. No.: 16/652,674

(22) PCT Filed: Oct. 25, 2018

(86) PCT No.: PCT/EP2018/079349
§ 371 (c)(1),
(2) Date: Mar. 31, 2020

(87) PCT Pub. No.: WO2019/081679
PCT Pub. Date: May 2, 2019

(65) Prior Publication Data
US 2020/0253538 A1    Aug. 13, 2020

(30) Foreign Application Priority Data

Oct. 25, 2017 (SE) .................................. 1751319-3

(51) Int. Cl.
*A61B 5/00*     (2006.01)
(52) U.S. Cl.
CPC ............ *A61B 5/443* (2013.01); *A61B 5/6833* (2013.01)
(58) Field of Classification Search
CPC ....... A61B 5/443; A61B 5/6833; A61B 5/444; A61B 5/0531
See application file for complete search history.

(56) References Cited

U.S. PATENT DOCUMENTS

| | | | | |
|---|---|---|---|---|
| 3,552,929 | A | * | 1/1971 | Neumayer ......... A61B 10/0064 D24/225 |
| 4,190,056 | A | * | 2/1980 | Tapper ................... A61B 5/415 600/307 |
| 4,557,271 | A | | 12/1985 | Stroller et al. |
| 5,203,327 | A | * | 4/1993 | Schoendorfer ...... A61B 5/6833 600/362 |

(Continued)

FOREIGN PATENT DOCUMENTS

| | | |
|---|---|---|
| EP | 2634556 B1 | 3/2018 |
| WO | 2014186894 A1 | 11/2014 |
| WO | 2017098518 A1 | 6/2017 |

OTHER PUBLICATIONS

International Search Report and Written Opinion, as issued in connection with International Patent Application No. PCT/EP2018/079349, dated Jan. 29, 2019, (8 pages).

(Continued)

*Primary Examiner* — David J Bolduc (57) ABSTRACT

The present disclosure relates to a device and method for detecting chemicals from tissue, such as skin, comprising at least a first detector (A) and at least a second detector (B), wherein the first detector (A) and the second detector (B) are the same type of detectors. An attachment portion (C3) including at least the first detector (A) and at least the second detector (B) separated by a defined distance, the attachment portion is configured to be attached on the tissue for detection of the chemicals.

19 Claims, 5 Drawing Sheets

(56) References Cited

U.S. PATENT DOCUMENTS

| | | | |
|---|---|---|---|
| 5,438,984 A * | 8/1995 | Schoendorfer | A61B 5/4845 600/584 |
| 5,441,048 A * | 8/1995 | Schoendorfer | A61B 5/415 600/362 |
| 5,445,147 A * | 8/1995 | Schoendorfer | A61B 10/0064 600/362 |
| 5,465,713 A * | 11/1995 | Schoendorfer | A61B 5/411 600/362 |
| 5,715,821 A | 2/1998 | Faupel et al. | |
| 5,817,012 A * | 10/1998 | Schoendorfer | A61B 10/0035 600/362 |
| 5,976,881 A * | 11/1999 | Klingner | G01N 31/22 436/1 |
| 6,585,646 B2 * | 7/2003 | Berlin | G01N 33/528 600/362 |
| 7,640,816 B2 * | 1/2010 | Horstmann | A61B 5/6833 73/863.21 |
| 10,746,663 B2 * | 8/2020 | Le | A61B 5/6833 |
| 2003/0065305 A1 * | 4/2003 | Higuchi | A61N 1/30 604/20 |
| 2003/0100819 A1 | 5/2003 | Newman et al. | |
| 2004/0106163 A1 * | 6/2004 | Workman, Jr. | A61K 49/0041 435/14 |
| 2005/0182307 A1 * | 8/2005 | Currie | A61B 5/1455 600/300 |
| 2006/0036138 A1 | 2/2006 | Heller et al. | |
| 2006/0062852 A1 * | 3/2006 | Holmes | A61B 5/15125 424/484 |
| 2007/0179522 A1 * | 8/2007 | Becker | A61F 13/00051 602/41 |
| 2008/0119707 A1 * | 5/2008 | Stafford | A61B 5/6833 604/27 |
| 2010/0191141 A1 | 7/2010 | Aberg | |
| 2011/0301441 A1 * | 12/2011 | Bandic | A61B 5/0537 600/306 |
| 2011/0306878 A1 * | 12/2011 | Desimone | A61N 1/306 600/431 |
| 2012/0130212 A1 * | 5/2012 | Pluta | A61B 5/14532 600/345 |
| 2012/0190952 A1 * | 7/2012 | Stafford | A61B 5/14503 600/345 |
| 2012/0321759 A1 * | 12/2012 | Marinkovich | A61B 5/442 356/402 |
| 2013/0079605 A1 * | 3/2013 | Bandaru | A61B 5/1486 600/347 |
| 2014/0350882 A1 * | 11/2014 | Everett | A61B 5/445 702/98 |
| 2016/0022985 A1 * | 1/2016 | DeSimone | A61N 1/0428 604/20 |
| 2016/0058342 A1 * | 3/2016 | Maiz-Aguinaga | A61B 5/14514 600/345 |
| 2016/0120458 A1 | 5/2016 | Yamada et al. | |
| 2016/0256070 A1 * | 9/2016 | Murphy | A61B 5/14517 |
| 2017/0156615 A1 * | 6/2017 | Shirazi | A61B 5/0205 |
| 2017/0325724 A1 * | 11/2017 | Wang | A61B 5/14532 |
| 2019/0069815 A1 * | 3/2019 | Burnes | A61B 5/7278 |
| 2019/0142318 A1 * | 5/2019 | Diebold | A61B 5/6833 600/575 |
| 2020/0375466 A1 * | 12/2020 | Ras | A61B 5/443 |

OTHER PUBLICATIONS

Search Report as issued in connection with Swedish Patent and Registration Office application No. 1751319-3 dated Apr. 26, 2018.

* cited by examiner

DEVICE AND A METHOD FOR DETECTION OF CHANGES IN TISSUE

TECHNICAL FIELD

The present disclosure relates to a detective device, and a method for detecting chemical substances, such as metabolites, emanating from tissue, such as in a gas or a fluid form. In particular the device and method relates to monitoring changes in tissue.

TECHNICAL BACKGROUND

The skin is the largest organ of a human being and is a vital part in several aspects. The malignant melanoma is a type of cancer where the incidence rapidly grows causing deaths and load to health care functions worldwide. There are very few ways of detecting malignant changes on skin such as malignant melanoma, basal cell carcinoma (BCC) or squamous cell carcinoma (SCC) where the two later are less fatal than the first. Present methods are often inaccurate, subjective and expensive as being done by physicians.

The most common way is to visually determine the likeliness of a visible spot to be malign or not and if a spot with a certain likeliness by visual inspection seems to be malign or is suspected to be malign there will be a sample cut out to be examined by a doctor or similar with skill to evaluate the sample being malign or not by the use of a microscope and sample preparation facilities. There is however a high level of uncertainty of determination whether a sample is or contain malign cells or not as it may come down to very few malign cells among healthy cells reducing the ability to detect of the malign. It is also required to, except for the skill to identify the cells, also have sample preparation, reducing the number of sites where possible diagnoses can be set to a small number. The process is invasive and requires for the purpose educated and trained personnel to extract samples. There are risks related to invasive processes such as risk for infections.

Another really invasive solution, which is intended for extraction of fluids through the skin, is described in US2017127990, where body fluids such as blood is by applied vacuum sucked out by a device using microneedles.

There are also some technologies based on image, analysis where an image of a suspected spot will with certain likeliness determine whether a spot is malign or not. There are several different solutions utilizing image analysis where some are just straight from a photographic image in natural light and some uses such as near-infrared (NIR) incident light to a spot on the skin that is suspected to be malign and where light adsorption and reflection can indicate a malign or healthy state due to changes in properties of the cells. This process is non-invasive and thereby less hazardous than the above mentioned.

SUMMARY OF THE INVENTION

An objective of the present invention is to alleviate at least some of the drawbacks of the prior art. This and other objects, which will become apparent in the following, are accomplished by a detective device, chemical detector system and a method of use of the device, as defined in the accompanying independent claims.

All living cells transform chemical substances in the metabolic processes and some metabolic pathways are specific to each type of cell dedicated to individual purposes. When cells are subject to change from being healthy cells to another state, such as cancerous cells, changes of the metabolism and subsequently change of emission of chemical substances as metabolites from the cells takes place and are traceable and indicators of diseases. The present invention solves a problem and relates to a method and a design to detect changes in tissue, such as skin. The changes may be due to cancer, such as skin cancer, such as malignant melanoma, basal cell carcinoma, or squamous cell carcinoma, by a non-invasive method based on chemical detection and chemical reaction of emission of evaporating metabolites emanating from skin and that are specific to the type of change of tissue, such as cancerous cells. The present method and device preferably relates to a non-invasive device and method of use thereof.

The invention can most likely be used to improve survival rate for patients with cancer, such, as skin cancer, such as malignant melanoma, as detection can be made in a more cost efficient and simplified manner at early stages by suspicion compared to traditional other methods. Other applications can be to improve also other dysfunctions in tissue such as allergic reactions or other diseases. Examples, of other diseases may be diseases due to Bacteria or viruses. The invention increases significantly the ability to detect changes in tissue, such as skin cancer, such as malignant melanoma, basal cell carcinoma, or squamous cell carcinoma, at early stages by a simple method, hence minimizing or reducing the risk for tumors to spread by metastases.

According to one aspect of the disclosure, a device for detecting chemicals from tissue, such as skin, is described. The device, may include at least a first detector and at least a second detector. The first detector and the second detector may be the same type of detectors, such as being identical. An attachment portion may include at least the first detector and at least the second detector. The first and second detector which may be separated by a defined distance. The attachment portion may configured to be attached on the tissue for detection of changes in the tissue.

In some examples of the disclosure, the first detector and the second detector may be configured to detect changes in the tissue based on detection of the emitted chemicals from the tissue.

In some examples of the disclosure, the attachment portion may be configured to be attached to different portions of the tissue, wherein the first detector may be configured to be positioned over a first tissue portion, which is suspected, such as visually suspected, to be affected by a disease. The second detector may be configured to be positioned over a second tissue portion of healthy tissue, such as visually healthy tissue.

In some examples of the disclosure, the first detector and the second detector may be configured to detect changes in tissue based on chemical detection from the tissue by detecting differences in a response between the first detector and the second detector.

In some examples of the disclosure, the chemical detection of the first detector and of the second detector may be by detection of changes in electrical or optical properties, or by detection of changes in chemical adsorption, or a combination thereof.

In some examples of the disclosure, the chemical detection of the first detector and of the second detector may be by detection of changes in emission of chemical compounds from tissue.

In some examples of the disclosure, the first detector and the second detector may be including an adsorbent, such as a polymer.

In some examples of the disclosure, the first detector and the second detector may include a material configured to be oxidized by an emanating metabolite from changes in the tissue.

In some examples of the disclosure, the material may be a metal, such as copper, silver or iron.

In some examples of the disclosure, the material may be a foil, powder, or a thin, layer.

In some examples of the disclosure, the material of detector may be divided in to two sections. A first section may be configured to contact the emanating metabolite. A second section may be chemically passivated.

In some examples of the disclosure, the first section of the first detector may be smaller than the second section of the first detector.

In some examples of the disclosure, the material may have a detection surface configured to facing the tissue.

In some examples of the disclosure, the material may have a detection surface configured to facing away from the tissue and towards an optically transparent area. The material may be at least partially circumscribed by an area permeable to the emanating metabolite. The first detector and the second detector, each may include a chamber, partly formed by the detection surface and the optically transparent area, to provide for the emanating metabolite to be collected, in and for contacting the detection surface.

In some examples of the disclosure, the optically transparent area of each chamber of the first detector and the second detector may be configured for inspection of the detection surface.

In some examples of the disclosure, the attachment portion may be two attachment portions merged together.

In a further aspect of the disclosure, a method of detecting changes in tissue is described. The method including, attaching an attachment portion which includes at least one first detector and at least one second detector. The first and second detectors may be arranged at a defined distance from each other. The first detector and the second detector may be the same type of detectors, such as being identical. The method may further include, detecting changes in tissue by detecting a difference in detector response between the first detector and second detector.

In one example of the method, the detection of changes may be by chemical detection. The chemical detection of the first detector and of the second detector may be by detection of changes in electrical or optical properties, or by detection of changes in chemical adsorption; or a combination thereof.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION OF THE DISCLOSURE

The present innovation relates to a solution and a mechanism that by the disclosure increases the ability to detect changes in tissue properties, such as skin properties, like skin cancer, malignant melanoma. The disclosure is applicable to various changes in skin properties as metabolism changes by various diseases and thereby the emission of metabolites.

The disclosure is based references, where each measurement relates to another for relative measurement rather than only absolute measurements. Measuring incorporating more than one measurement spot can be generally used and is possible to incorporate by slight modifications for other applications.

The disclosure can also be used with other designs, but still with more than one spot and where indications that is relative between more than at least two spots.

The disclosure can be designed for various detection methods based on different detection solution such as but not limited to:

Change or no change in electrical properties in different spots of a chemical substance applied in the spots being exposed to a defined metabolite chemical substance emanating from tissue or not. Such electrical properties can be change of resistance and or impedance and or inductance.

Change or no change in optical properties in different spots of a chemical substance applied in the spots being exposed to a defined metabolite chemical substance emanating from tissue or not. Such optical properties can be change of transparency and, or reflectance and or refringence and or color and or fluorescence. Change or no change in electrical and optical properties in different spots as mentioned above combined.

One solution can be to detect the presence of a substance, such as a gas or fluid, such as a liquid, emanating from a diseased tissue area, such as a diseased skin area, such as malign melanoma, that may create changes in a material. Such a substance may be hydrogen peroxide ($H_2O_2$), Dimethyl Disulfide, or a Sulphur containing chemical substance, which may oxidize metals, for example, iron, copper, and silver. The temperature range for detection of a skin disease, such as an area with suspected skin cancer, such as malign melanoma, is typically in the range of 280 K to 323 K, normally around 305 K being the normal skin surface temperature.

The substance may not only be in a fluid phase. In some examples, the substance may be transported with a fluid, such as sweat. Should the substance be in a more solid form when on the tissue, a transport fluid may for example be applied to the tissue to solve the substance and have it contacting the detectors. Hence the disclosure is not limited to only detect substances, such as metabolite, in a gas phase. Even though the gas phase may be the main example given, the disclosure is not limited to this and most of the detectors would function the same way as for gas if the substance was in a fluid form, such as absorbers or metal etc. Only slight modification may be needed to have the detectors configured to detect a substance in a fluid or fluid phase, rather than as gas. The main adaption is the arrangement of the detectors to have the detectors either touching the tissue or have the fluid sucked towards the detectors. For example the distance between the detector and the tissue, as illustrated in FIGS. 2B, 2B and 4 to 6, may be reduced or eliminated. Alternatively the space may be filled with a material or capillaries for transporting the fluid to the detectors.

Additionally and/or alternatively, the detection may also be based on changes to other metal properties. The difference between changes in the spot that is placed over a suspected tissue area, such as a skin area with suspected skin cancer, such as malign melanoma, and at least one second reference spot on a distance from the first spot may indicate a difference in emission of substances. Hydrogen peroxide is the second most reactive chemical giving a high sensitivity for a first spot combined with high specificity on least one second reference spot on a distance from the first spot.

When using a metal as the detector, the surface used as an indicator may be made from a foil, powder, or a layer applied on a substrate provided with a pattern where most of the surface is chemically passivated, such as being covered by an optically transparent layer, for example lacquer, that prevents gas emanating from the tissue to come into contact with the covered part of the surface. The uncovered surface may be less than 50% of the total surface of the indicator, preferably around 1 to 30%, such as 1 to 20%, such as 1 to 10%, such as 1 to 5%. The rest of the surface may have a pattern with a single line, a plurality of lines, spots or other small area structures exposing the metal surface, so if a reagent chemical substance from the tissue reaches the foil or layer, only the small pattern may be chemically affected by the substance.

Providing a surface where the uncovered part of the indicator is smaller than the covered part, may result in a color change which may have a visually detectable pattern with high contrast between the covered parts of the surface and, parts of the surface exposed to a chemical substance from a suspected tissue area, such as a skin area with suspected skin cancer, such as malign melanoma. Additionally, and/or alternatively, a surface area of an indicator which may be exposed to a chemical substance being smaller than a covered area of the same indicator, may also provide increased sensitivity and decreased detection time. Increased sensitivity makes it possible to detect a tissue disease, such as skin cancer, at an earlier stage.

Another solution may be to detect changes in emission of chemical compounds from tissue. The compounds may relate to metabolic processes and may include, for example, hydrogen peroxide ($H_2O_2$), Dimethyl Disulfide, or a Sulphur containing chemical substance. Detect changes in emission may be conducted by having an adsorbent to adsorb emitted chemical compounds from at least two different locations A and B and to thereafter desorb the chemical substances from A and B and have the composition analysed and determined by instruments like gas chromatography. Differences in detected and quantity of chemical substances indicate differences in adsorbed chemical substances between A and B and can be compared with references of chemical substances to determine likeliness of a patient having a certain disease or not. The adsorbent may be a polymer, for example, polydimethylsiloxane, divinylbenzene, carboxen, or polyacrylate or combinations thereof or other such as activated carbon or other chemical substance with adsorption and desorption properties. The adsorbent may also be, for example, a porous grain or granular material for example charcoal or activated carbon.

The current disclosure describes a device for a chemical detector system, comprising at least one first attachment portion including at least one first detector and at least one second attachment portion including at least one second detector. Alternatively, the first attachment portion and the second attachment portion may be merged together to form at least one joint attachment portion, which includes at least one first detector and at least one second detector, for detection of changes in tissue, such as skin. The first detector and the second detector are the same type of detector having the same configuration, i.e. the first and second detectors are similar or identical, The attachment portions may be configured to be attached, to different portions of the tissue. The portions related to the first detector may be configured to be placed over a first tissue portion which may be visually suspected to be affected by a disease. Further, the second detector is configured to be placed over a second tissue portion, which may be visually healthy tissue.

The visually suspected tissue portion may be affected by skin cancer, such as malignant melanoma, basal cell carcinoma, or squamous cell carcinoma. Additionally, the second skin portion may be visually healthy tissue. The visually healthy skin portion may function as a reference. In some examples, the first detector and the second detector may part of a single attachment portion, where the first and second detectors are separated by a s defined distance. In this way the second detector may be arranged outside of the suspected tissue portion, but still in in close proximity to the same. This has the advantage that the tissue properties and characteristics may be similar compared to if the attachment portions where attached further away or at different parts of the body. Similar tissue properties and characteristics may have a role should the suspected tissue portion be healthy, and may lower the risk of positive results when the suspect tissue is healthy. Also, the amount and type of substances, such as metabolites, emanating from the tissue which may not be related to a disease may be similar when the detectors are in close proximity to each other. Hence reducing the tissue variations factors in the result. The substances may be a gas or a fluid, such as a liquid, or a substance transported with fluid.

The detection of changes in tissue, due to a disease such as skin cancer, by chemical detection may be obtained by determining a difference in detector response between a detection at, the first detector and a detection at the second detector. The chemical detection of the first detector and of the second detector may be a detection of changes in electrical or optical properties, or by detection of changes in chemical adsorption, or any combination thereof. Additionally, and/or alternatively, in some examples, the chemical detection of the first detector and of the second detector may be by a detection of changes in electrical or optical properties, or any combination thereof, such as detection of changes in electrical and optical properties in combination. The detection of changes in electrical properties may be changes in for example resistance, impedance, or inductance, or any combination thereof. The detection of changes in optical properties may be for example transparency, reflectance, refringence, color, or fluorescence, absorption, or any combination thereof.

While certain illustrative examples of the disclosure have been described in particularity, it will be understood that various other modifications will be readily apparent to those skilled in the art without departing from the scope of the appended claims. Accordingly, it is not intended that the scope of the claims appended hereto be limited to the description set forth herein.

Additionally, although individual features may be included in different examples, these may possibly be combined in other ways, and the inclusion in different examples does not imply that a combination of features is not feasible. In addition, singular references do not exclude a plurality.

The term "detect", detecting" and "detection" are to be seen as including terms such as measure, note, determine, observe, attain, achieve, and obtain as well. One purpose of the present disclosure is to provide awareness of that a difference is present.

The term "change", "changes" or "changing" are to be seen as including terms such as variations, and difference.

The terms "a", "an" does not preclude a plurality. Reference signs in the claims are provided merely as a clarifying example and shall not be construed as limiting the scope of the claims in any way.

The term "skin" relates to is the soft outer tissue covering vertebrates. Mammalian skin is composed of two primary layers; the epidermis, which provides waterproofing and serves as a barrier to infection, and the dermis, which serves as a location for the appendages of skin.

The term "adsorbents" relates to a material with the ability to adhesively attach atoms, ions or molecules from a gas, a fluid or solid dissolved in a fluid to its surface. The absorbents are used usually in the form of spherical pellets, rods, moldings, or monoliths with a hydrodynamic radius between 0.25 and 5 mm. They must have high abrasion resistance, high thermal stability and small pore diameters, which results in higher exposed surface area and hence high capacity for adsorption. The adsorbents must also have a distinct pore structure that enables fast transport of the gaseous vapors. Most industrial adsorbents fall into one of three classes:

Oxygen-containing compounds—Are typically hydrophilic and polar, including materials such as silica gel and zeolites.

Carbon-based compounds—Are typically hydrophobic and non-polar, including materials such as activated carbon and graphite.

Polymer-based compounds—Are polar or non-polar functional groups in a porous polymer matrix.

The disclosure is further described with references to the drawings that show parts of a device such as the disclosure. In order that the manner in which the above recited and other advantages and objects of the disclosure are obtained will be readily understood, a more particular description of the disclosure briefly described above will be rendered by reference to specific examples thereof which are illustrated in the appended drawings.

Figure 1:
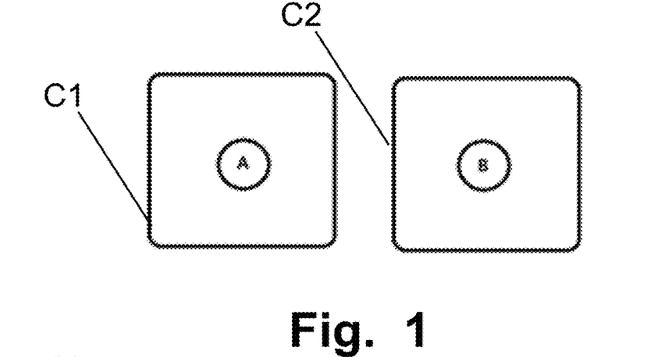
FIG. 1. Illustrates one example of the present disclosure from a top view of the device and/or detector system, wherein two detectors are arranged on separate attachment portions.

The same reference numerals have been used to indicate the same parts in the figures to increase the readability of the description and for the sake of clarity. The figures are not made to scale, and the relative dimensions of the illustrated objects may be disproportional. Understanding that these drawings depict only typical examples of the disclosure and are not therefore to be considered to be limiting of its scope, the disclosure will be described and explained with additional specificity and detail through the use of the accompanying drawings in which:

FIG. 1 illustrates an exemplary device according to the disclosure. The illustration is a top view of the device and/or detector system, showing an attachment portion C1 and an attachment portion C2. The attachment portions are configured to be attached to tissue, such as skin of a human or an animal. The first attachment portion C1 is including a detector A and the second attachment portion C2 includes a detector B. The positions of an area/detector A that is placed over a suspected area of changes in the tissue, such as skin, and where another area/detector or areas/detectors B are positioned where it is not suspected to be any changes in the tissue. The area/detector B may then be used as a reference in relation to area/detector A and where the areas may be separately attached.

The attachment portion may be configured to be reversibly attachable to respective tissue portions. This may be done by using an adhesive or using negative pressure. The attachment portions C1, C2 are adhesively attachable to respective tissue portions, by a sheet of preferably non-transparent polymer, aluminum (Al) foil or other foil material with an adhesive layer or self-adhesive layer on one side of the sheet. Additionally, and/or alternatively the attachment portions C1, C2 may be attachable to respective tissue portions by negative pressure. Negative pressure may help to increase the circulation through the tissue.

The attachment portions C1, C2 may have any type of geometric shape, such as oval, circular, donut, rectangular, square, truncated square, rhombic, star, heart, diamond, ellipse, kite, triangular, trapezium, parallelogram, any polygon such as pentagon, hexagon, heptagon, octagon, nonagon, or decagon or other shaped area. The attachment portions C1, C2 may have an area of between 0.1 mm$^2$ to 0.5 m$^2$. Further, the attachment portions C1, C2 may have the same sizes compared to each other, or the attachment portions C1, C2 may have a ratio of between 1:10 to 10:1.

The first and second detectors A, B may each have a size which may be smaller than the sizes of respective the attachment portions C1, C2. In some examples, the first and second detectors A, B may have a size between 0.1 mm$^2$ to 0.5 m$^2$, such as 1 to 100 mm$^2$, such as 1 to 50 mm$^2$, such as about a general size of a visually suspect skin cancerous mark, e.g. about 1 to 40 mm$^2$, such as about 25 to 40 mm$^2$ such as about 36 mm$^2$. Additionally, and/or alternatively, in some examples may the first and second detectors have the same size or have a well-defined difference in size compared to each other. For example, the detectors may have a ratio of between 1:10 to 10:1 or other predetermined.

Additionally, to the described detectors, the first and second attachment portion may include further sets of detectors for detection of another type of diseases then may be detected by the first and second detector A, B. For example, a second set of detectors may be configured to detect neoplastic and/or inflammation. The emanated chemical compound may be nitric oxide (NO) and/or nitrogen dioxide (NO$_2$). The detectors may here be made from, for example, a ceramic consisting mostly of one or more crystalline and/or vitreous oxide or oxides, usually oxides of one or more metallic and/or semi-conducting element or elements, such as silicon, sodium, aluminum, magnesium, calcium, magnesium, titanium, zirconium, lithium. Detection of inflammation may be used as a further indication when detecting cancer.

The device or a chemical detector system is intended for single time usage and disposable after use. Alternatively, in some examples the device or the chemical detector system, may be intended for reuse after an exchange of the used first and second detectors A, B.

Figure 2A:
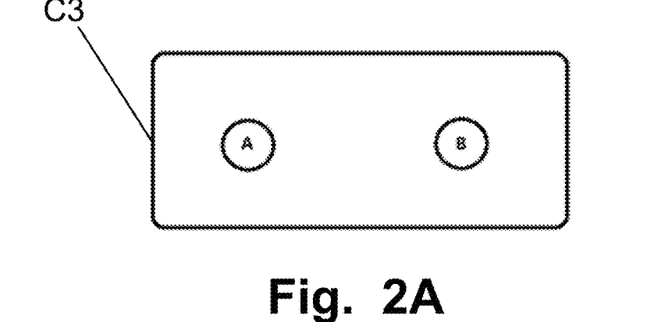
FIG. 2A. Illustrates another example of the present disclosure from a top view of the device and/or detector system, wherein two detectors are arranged on the same attachment portion.

FIG. 2A illustrates an exemplary device according to the disclosure. The device may include the same features or configurations as described herein above in relation to FIG. 1. FIG. 2 is illustrating the device and/or detector system from a top view, showing an attachment portion C3, including a first detector A and a second detector B. A first area/detector A may be arranged on or in the attachment portion C3 so that it may be placed over a suspected area of changes in tissue, such as skin, such as skin cancer, such as malign melanoma. A second areas/detectors B may be arranged in or in the attachment portion C3, and configured so that the detector B may be positioned over tissue where there is no suspicion of any changes in the skin. The second areas/detectors B may then be used as a reference in relation to the first areas/detectors A.

When arranged on a single attachment point C3, the first and second detectors A, B may be separated by a fixed distance. The distance may be defined so that the at least one second detector B may be arranged outside of the suspected tissue portion but still in in close proximity to the same. A typical distance may be around 10 to 50 mm between two detectors, but may be shorter or longer. This has the advantage that the tissue properties and characteristics may be similar when looking at healthy tissue, compared to if the attachment portions where attached further away or at different parts of the body. Similar tissue properties and characteristics may have a role should the suspected tissue portion be healthy, and may lower the risk of positive results when the suspect tissue is healthy. Also, the amount and type of gases emanating from the tissue which may not be related to a disease may be similar when the detectors are in close proximity to each other. Hence reducing the tissue variations factors in the result. It may also reduce variations in the measured results that may be derived from the manufacturing process.

Figure 2B:
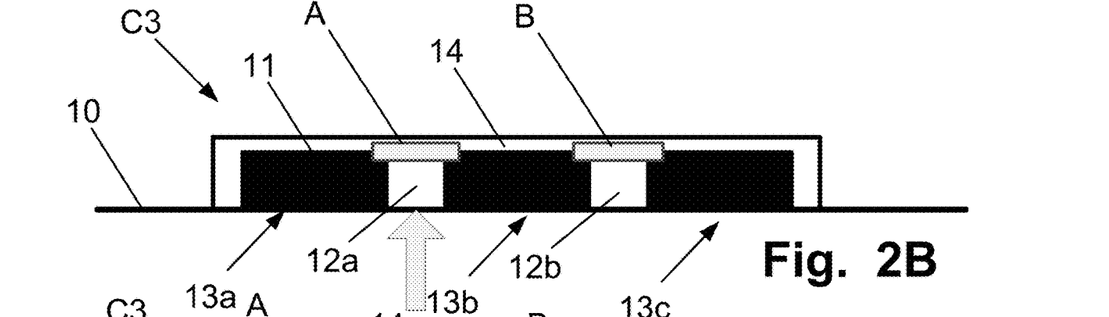
FIGS. 2B and 2C illustrating examples of cross-section of the device and/or detector system illustrated in FIGS. 2A and 2B?
Figure 2C:
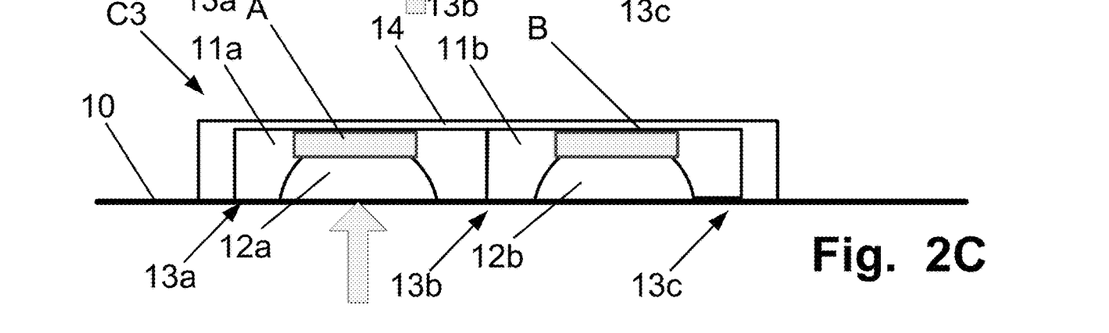

The two detector areas may also be combined into a long single strip, for example made of a material to be oxidized, where one end may be the detector A to be arranged over a suspected area, and the other end of the strip may be the second detector B. The chemical reaction may then be obtained as a gradient with a higher detection rate around detection area A and then decreasing towards detector area B FIGS. 2B and 2C illustrating examples of cross-sectional views of the device illustrated in FIG. 2A.

FIG. 2A is illustrating an attachment portion C3, such as a patch. The attachment portion C3 is made of a sheet of material 11, such as a polymer, aluminum foil or other foil material. The sheet may have an adhesive layer on one side for attaching removing the patch from tissue. In some examples is the sheet made from a plurality of layers. If a polymer sheet is used to for the patch, or attachment portion C3, the material may be the same as used for wound dressing or wound care. In the materials may at least two holes be formed, 12a, 12b, one hole for each detectors A, B. The holes 12a, 12b may go completely through the material 11, such as a through hole, or only partially through, such as a blind hole. The holes, 12a, 12b may have any shape, such as cylindrical, partly spherical, partly ellipsoidal, rectangular, oblong, truncated cone, etc.

The at least two detectors A, B may be arranged on top of the holes, 12a, 12b, against an upper inner surface of the holes 12a, 12b or between layers of the material 11. In examples, where the detectors A, B may be arranged on top of a through hole 12a, 12b, a further layer 14 may be arranged on top of the sheet 11. The top layer 14, may be non-transparent or transparent, and may be extend further than the sheath 11 for further attaching the device to the tissue 10.

The space 12a, 12b obtained between the detectors A, B and the tissue 10, may function as chambers, and may be filled with air or a gas permeable material. In some examples, when a gas permeable material is used, the material may be polymer or silica based. Additionally, in some example may the gas permeable material be selective to certain gases.

When the patch or attachment portion C3 is attached to the tissue 10, the adhesive at the areas 13a, 13b, 13c around the holes 12a, 12b attaching the patch or attachment portion C3 provides independent chambers separated by a distance from each other. The distance may be fixed and pre-determined. The adhesive attaching the patch to the tissue 10, especially at the area 13b between the detectors A, B prevents emanating substance from suspect tissue, indicated by an arrow, to reach the chamber of the detector B positioned over healthy tissue, such as visually healthy. The responses of the two detectors may thereby be independent of each other. The adhesive may be evenly distributed under the whole bottom surface of the illustrated device. Alternatively, in some examples, the adhesive is only arranged surrounding the opening of the holes 12a, 12b, forming two separate attachment portions, but still separating the detectors to avoid substances from the suspect tissue to reach the detector arranged over healthy tissue.

FIG. 2C is illustrating an attachment portion C3, such as a patch, made from two separate portions 11a, 11b, such as separate attachment portion C1, C2 which have been joined or merged together to form a non-separable single attachment portion C3. In other aspects, the illustrated device may function as the device illustrated in FIGS. 2A and 2B. FIG. 2C is illustrated with holes 12a, 12b shaped as partial spherical, but other shapes may be possible, such as cylindrical, partly spherical, partly ellipsoidal, rectangular, oblong, truncated cone, etc.

Figure 3:
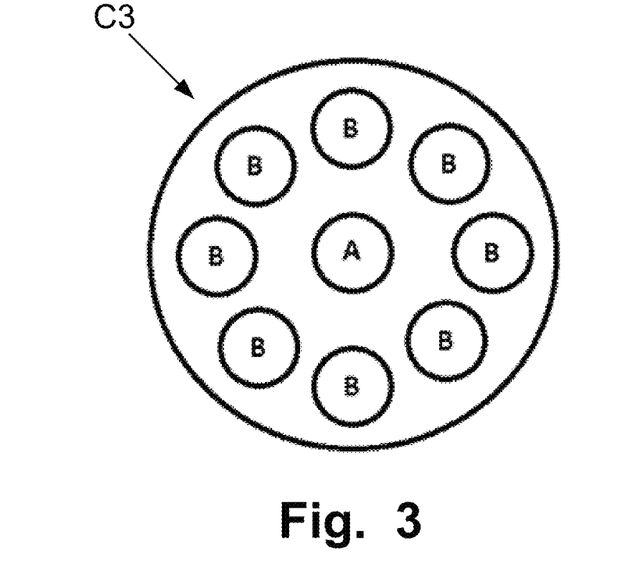
FIG. 3. Illustrates one example of the present disclosure from a top view of the device and/or detector system with multiple detectors to be arranged on healthy tissue.

FIG. 3 illustrates one example of a device according to the present disclosure. FIG. 3 is illustrating the device and/or detector system from a top view, showing an attachment portion C3, such as a single attachment portion, including at least a first detector A and at least two second detectors B, such as a plurality of detectors B. The positions of an area/detector A allows it to be placed over a suspected area of changes in the tissue, such as skin, such as skin cancer, such as malign melanoma. The second areas/detectors B may be positioned where there is no suspicion of any changes in the tissue and where the second detectors B then may be used as a reference in relation to the first detector A.

The attachment portion C3 may have a rectangular or circular or other shaped. The attachment portion C3 may be made from a sheet of preferably non transparent polymer, aluminum foil or other foil material with adhesive layer on one side to have the sheet attachable and removable to tissue.

The circular areas/detectors A respectively B are spot, areas comprising either optically transparent windows of preferably a optically transparent polymer provided with a reagent that change its properties and or provides a space where substances can be captured by any means and from exposure of chemical compounds emanating from skin surface emission. The at least two areas/detectors A and B will by chemical influence to the reagents be able to differentiate emission from then possible difference in emission where emission from as example a skin area exposed to A with suspected malign melanoma differ from similar area separated from the other exposed to area/detector B or have devices that captures, adsorbs, the mentioned chemical substances for later analyses. Adsorption, of emanating substances such as metabolites can be made by solid phase extraction materials or Solid Phase Micro Extraction (SPME), for further analyzes by gas chromatography or other laboratory equipment intended for detection and quantification of chemical substances. If two or more areas A or B are used where one area A or B is where the skin disease is suspected and at least one other area A or B where it is not expected to be affected by the disease.

In one example, the device may be configured to detect the presence of $H_2O_2$, Hydrogen peroxide, Dimethyl Disulfide, or a Sulphur emanating as metabolites from diseased tissue, especially from skin cancer, such as malignant melanoma by oxidizing a metal foil, a thin layer of metal or a metal powder or other substance that easily reacts as with $H_2O_2$, Dimethyl Disulfide, or a Sulphur containing chemical substance to create a visually or by other means measurable change in electrical, visual or optical properties and differences between area/detector A and area/detector B. The metal may for example be, iron, copper, or silver.

Figure 4:
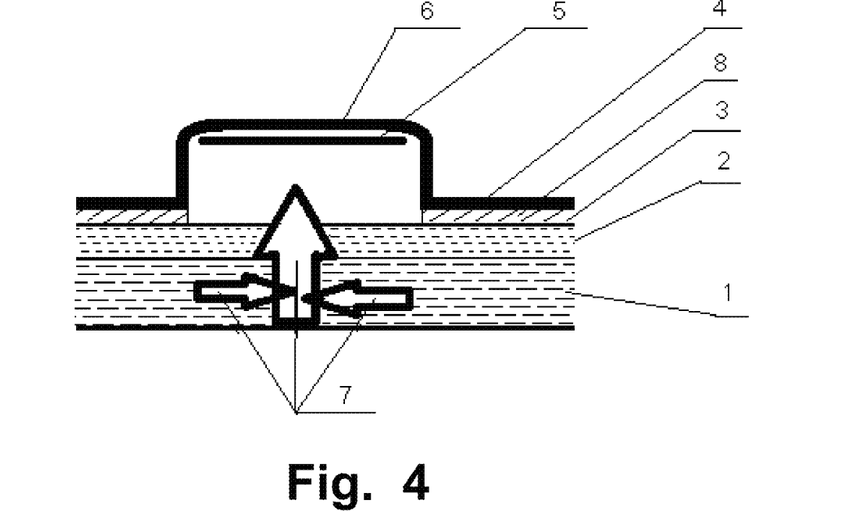
FIG. 4. Illustrates one example of the present disclosure from a side view of the device and/or detector system being attached to the skin.

FIG. 4 illustrates one example of the present disclosure from, a side view of the device and/or detector system. FIG. 4 is illustrating at least a section of an attachment portion C1, C2, C3 of the device and/or detector system being attached to the skin. Reference to numbering: Dermis (skin deeper layer) 1, epidermis (skin outer layer) 2, border between adhesive layer and skin 3, carrier sheet 4, indicator/adsorbent 5, window for optical/visual indication 6, flow of metabolites (such as $H_2O_2$ or other) 7, self-adhesive layer 8.

Figure 5:
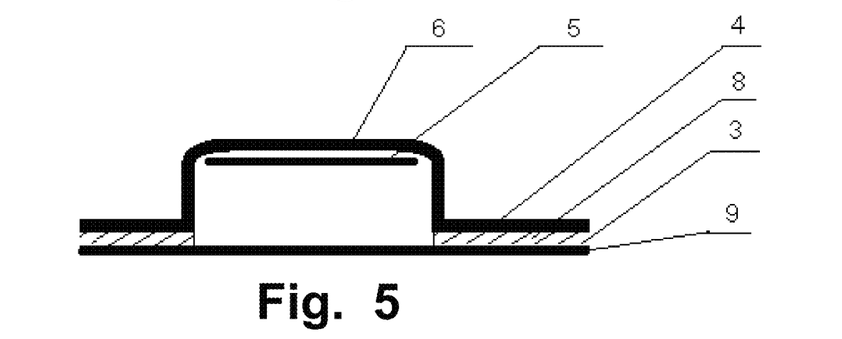
FIG. 5. Illustrates one example of the present disclosure from a side view of the device and/or detector system before use.

FIG. 5 illustrates one example of the present disclosure from a side view of the device and/or detector system. FIG. 5 is illustrating at least a section of an attachment portion C1, C2, C3 of the device and/or detector system before use. Reference to numbering: Border between adhesive layer and skin 3, carrier sheet 4, indicator/adsorbent 5, window for optical/visual indication 6, self-adhesive layer 8, removable protective sheet 9.

Figure 6:
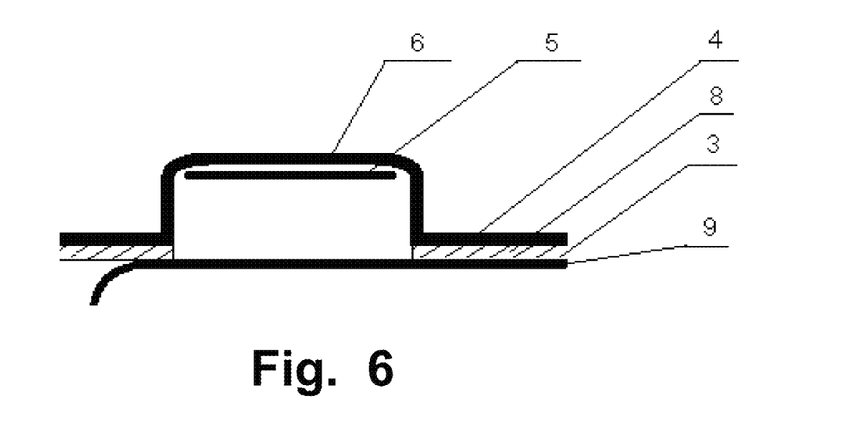
FIG. 6. Illustrates one example of the present disclosure from a side view of the device and/or detector system just about to be applied.

FIG. 6 illustrates one example of the present disclosure from a side view of the device and/or detector system. FIG. 6 is illustrating at least a section of an attachment portion C1, C2, C3 of the device and/or detector system device just about to be applied. Reference to numbering: Border between adhesive layer and skin 3, carrier sheet 4, indicator/adsorbent 5, window for optical/visual indication 6, self-adhesive layer 8, removable protective sheet 9.

In FIGS. 4 to 6, when using a metal surface as an indicator 5, the configuration may be done either as illustrated a detection surface to reach with the emanating chemical substance, such as a metabolite, is configures to configured to facing the tissue. In this configuration, there is a space between the detection surface of the indicator 5 and the tissue to which the attachment portion is positioned. After the detector system has been positioned on the tissue for a period of time such as second, minutes, hours or days, but normally around 15 min or up to 7 days depending on the type and stage of the disease, it will be removed and the first and second detectors A, B may be compared. In this configuration, since the device has to be turned around to be read, there may no use for the optically transparent window 6 apart from indicating where the detectors are located to help to arrange them at the correct position.

Alternatively, the detection surface may be configured to facing in a different direction than towards the tissue (not illustrated) for example in an opposite direction towards an optically transparent area. The indicator 5 may then be, at least partially, circumscribed by an area permeable to the emanating chemical substances. For example, could a perforated material, a mesh, or a gas permeable, material be arranged to at least partially circumscribe the indicator 5. Another option is to leave at least a portion circumscribing the indicator 5 open or hold the indicator by struts. In this configuration, each detector A and B includes a chamber, partly formed by the detection surface and an optically transparent area, to provide for the emanating metabolites to be collected in and contacting the detection surface. The optically transparent area may be used for visually inspecting the detection surface of the indicator 5.

Figure 7:
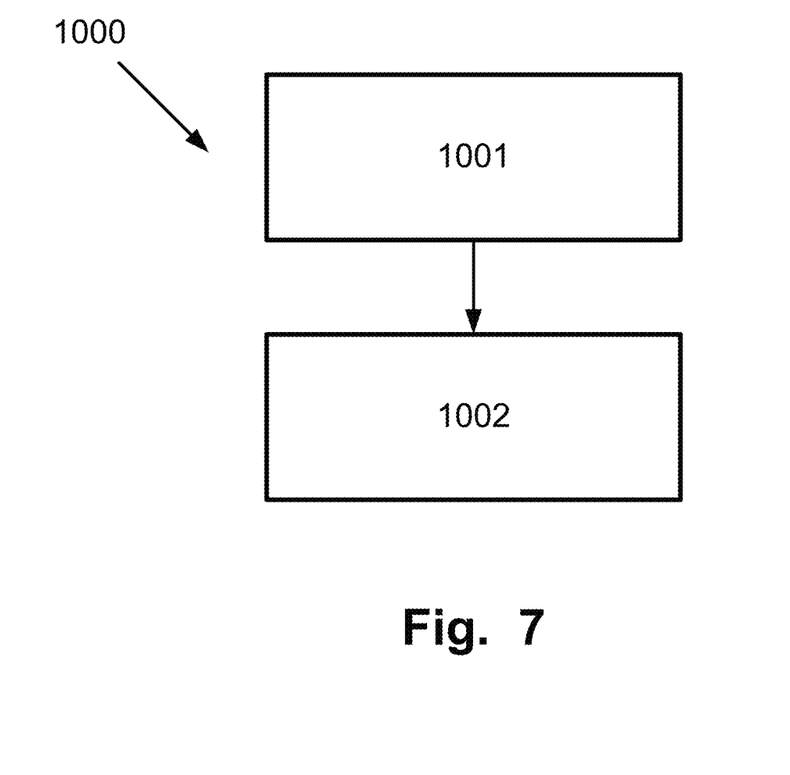
FIG. 7 illustrating a flow-chart of an exemplary method.

FIG. 7 is illustrating a method 1000 of detection of changes in tissue, such as skin. The method is completely non-invasive and includes attaching a patch on the tissue, such as the skin. The patch may be applied to a suspected tissue by the subject him/herself, as a home test. The patch may also be attached any hospital staff as part of an assessment of a suspected area. Since the patch is completely non-invasive and is only attached to the tissue, such as the skin, in accordance with provided instructions. There is no need for highly trained or specialized staff to carry out the steps of attaching and removing the patch, and the method does not provide a substantial health risk. The disclosed method may include:

Attaching 1001 an attachment portion C3 to a tissue area. The attachment portion C3 comprising at least one first detector A and at least one second detector B at a defined distance from each other. The first detector A and the second detector B are of the same type of detectors, such as being identical. The attachment portion C3 is arranged so that the first detector A is positioned over a visually, suspected tissue area, and the detector B over a visually, healthy tissue area.

Detecting changes in tissue by detecting a difference in detector response between the first detector A and the second detector B. This step may include the removal of the patch to be able to compare the two detectors A, B. The comparison could either be visually or by means of a detector system for reading the indicators. The detector system to be used depends on the type of detectors used for the patch. For example, in the case of using a metal to be oxidized, the detector system may be an optical system, such as a camera based system, for analyzing the detectors A, B to detect if there is a response in the detector A, positioned over the visually suspected area, compared to the detector B, positioned over the visually healthy tissue. Another option is to detect and analyze changes in the electrical properties due to oxidation. The patch may also be sent to a laboratory for analyzing the result. Hence the subject, such as a patient, may not need to be present during all of the steps, particularly at the detection and analyzing step when the patch has been removed from the subject, or patient.

If the chemical detection of the first detector A and of the second detector B is by adsorption and desorption for quantitative and qualitative analyze by such as gas chromatography with detectors such as, flame, mass spectrometry, ultra violet absorption or other.

In yet another example, the analysis is based on comparison of readouts between two or more detectors. It may not be necessary to identify single specific chemical substances/metabolites present in the detectors. It may just be enough to compare the conglomerated readouts from the different detectors by for example (fx) image recognition to find out that there is a difference between two detectors.

Figure 8A:
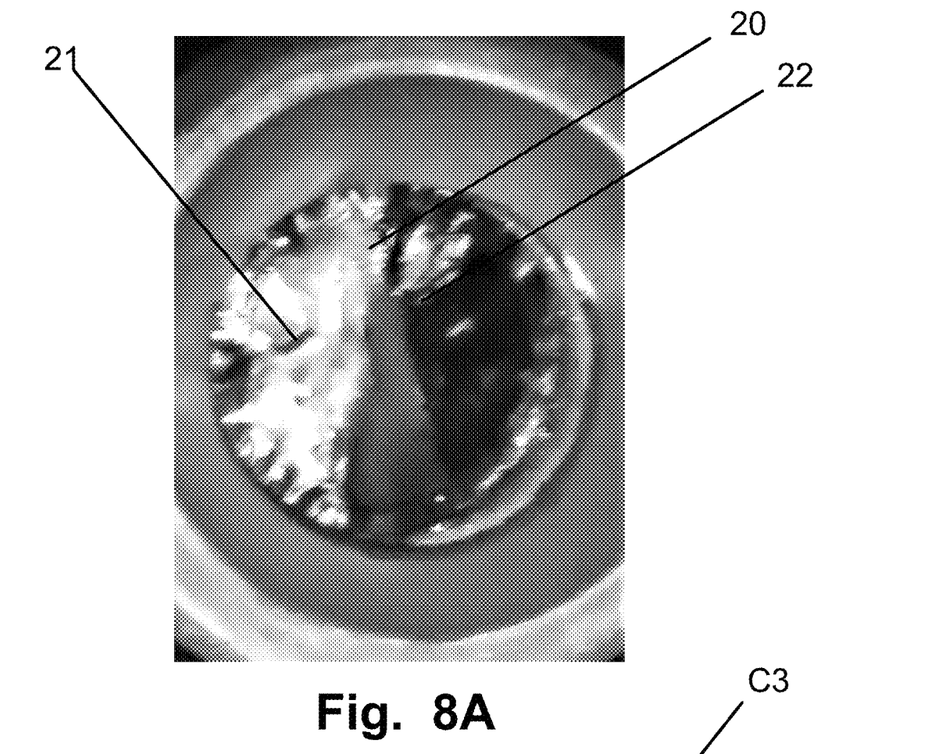
FIGS. 8A and 8B illustrating images from experiments.

The method may be generally used to detect variations in emission of chemical substances at a tissue site, such as at a skin site, probably being indicators of other skin disease apart from cancerous mentioned FIG. 8A is illustrating a detector 20 made from copper after being exposed Dimethyl Disulfide under gas conditions similar to what may be expected when attached to tissue. The device had one portion untreated 22, and another portion was chemically passivated 21, in this example by a lacquer. The untreated portion 22, oxidized and turned dark, as seen in the image. The chemically passivated portion 21 provides a higher visual contrast to the oxidized portion 22 compare if no passivated portion would have been provided. Similar result have been obtained with other metals; such as Iron or silver, depending on the exposure time as well as using other gases, such as hydrogen peroxide, or a Sulphur.

Figure 8B:
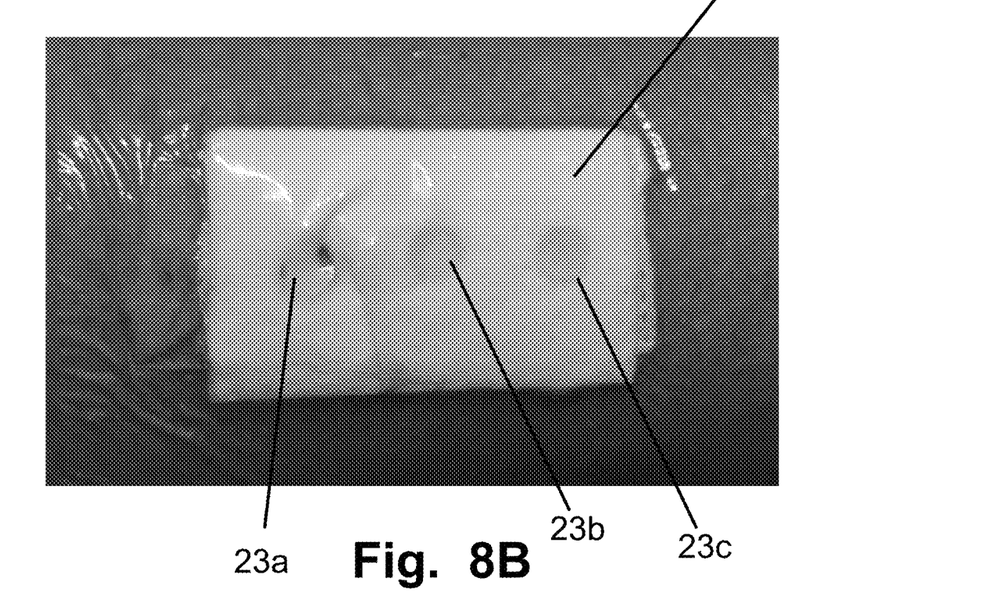

FIG. 8B illustrating a patch C3 on an arm with three detectors 23a, 23b, 23c made of metal. All detectors were arranged over tissue being visually healthy. The patch C3 was worn for three days and no indication was detected by any of the detectors 23a, 23b, 23c.

This indicates that healthy tissue does not give a response while some of the gases emanating from skin cancer does.

Figure 9:
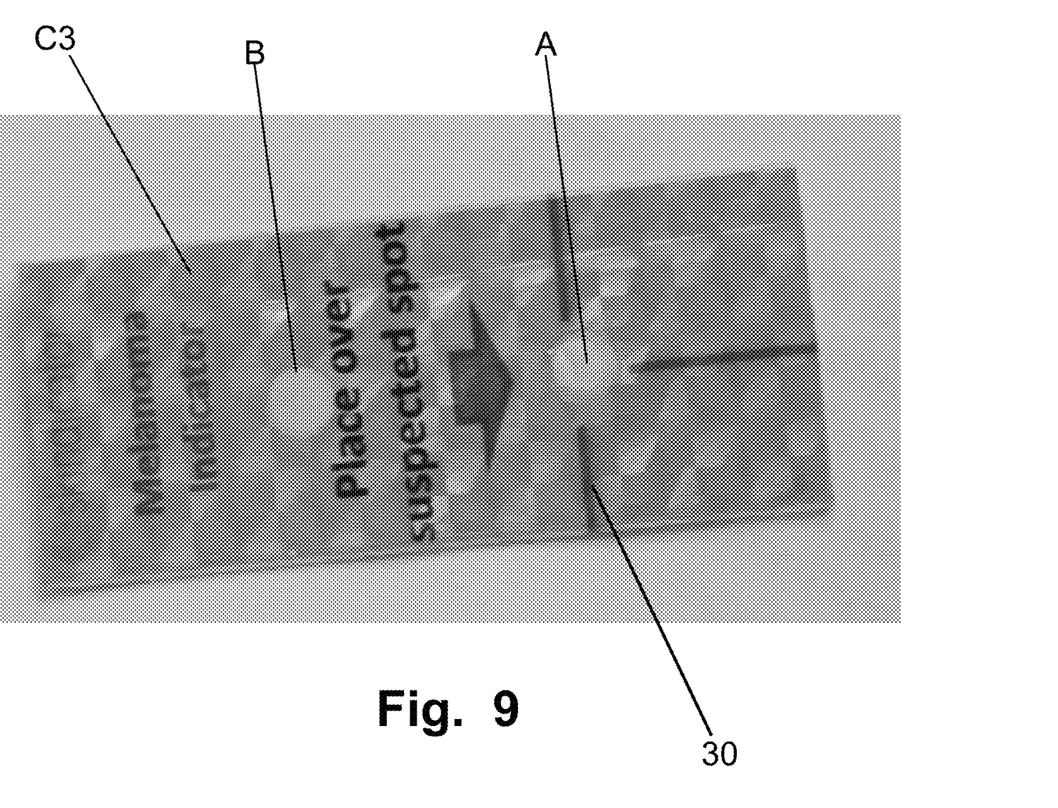
FIG. 9 illustrating an example of a device for detecting chemicals from tissue.

FIG. 9 illustrating an example of a device according to the disclosure seen from above. The device has an attachment portion C3, or patch. The device does further include at least two detectors A, B, wherein one of the detectors A, is configured to be arranged over suspect tissue. The device has marks 30, in this example similar to a hair cross but other alignment technics known to the killed person may be used, for aligning the detector A with the suspected mark on the tissue and lines drawn by the practitioner or the subject himself before attaching the device to the tissue. The detector A, B may be covered during use to minimize the psychological stress on the patient during detection.

The present disclosure has been described above with reference to specific examples. However, other examples than the above described are equally possible within the scope of the disclosure. Different method steps than those described, above, may be provided within the scope of the disclosure. The different features and steps of the disclosure may be combined in other combinations than those described. The scope of the disclosure is only limited by the appended patent claims.

The invention claimed is:

1. A device for detecting chemicals from skin tissue, the device comprises:
    at least a first detector and at least a second detector, wherein the first detector and the second detector are identical types of detectors, and wherein said second detector is a reference detector;
    an attachment portion including at least said first detector and at least said second detector separated by a defined distance, said attachment portion is configured to be attached on said skin tissue for detection of said chemicals; and
    wherein said first detector and said second detector are in fluid communication with said skin tissue and comprising a material configured to provide a measurable change in at least one of an electrical, a visual, and an optical property based on differences between the first detector and the second detector by an emanating metabolite from changes in dermis or epidermis due to a tumor.

2. The device of claim 1, wherein said first detector and said second detector are configured to detect changes in said dermis or epidermis due to a tumor based on detection of said emanating metabolite from said dermis or epidermis due to a tumor.

3. The device according to claim 1, wherein said attachment portion is configured to be attached to different portions of said skin tissue, wherein said first detector is configured to be positioned over a first skin tissue portion, which is suspected to be affected by a disease, and said second detector is configured to be positioned over a second skin tissue portion of healthy tissue.

4. The device according to claim 1, wherein said first detector and said second detector are configured to detect changes in dermis or epidermis based on emanating metabolite detection from said dermis or epidermis by detecting differences in a response between said first detector and said second detector.

5. The device according to claim 4, wherein the emanating metabolite detection of said first detector and of said second detector is by detection of changes in electrical or optical properties, or by detection of changes in chemical adsorption, or a combination thereof.

6. The device according to claim 4, wherein the emanating metabolite detection of said first detector and of said second detector is by detection of changes in emission of emanating metabolite from dermis or epidermis.

7. The device according to claim 1, wherein said first detector and said second detector comprises an adsorbent.

8. The device according to claim 7, wherein the adsorbent comprises a polymer.

9. The device according to claim 1, wherein said material is a metal.

10. The device according to claim 1, wherein said material is a foil.

11. The device according to claim 1, wherein said material of detector is divided in to two sections, a first section configured to contact said emanating metabolite, and a second section being chemically passivated.

12. The device according to claim 11, wherein the first section is smaller than the second section.

13. The device according to claim 1, wherein said material has a detection surface facing said skin tissue.

14. The device according to claim 1, wherein said material has a detection surface away from said skin tissue towards an optically transparent area, and wherein said material is at least partially circumscribed by an area permeable to said emanating metabolite and wherein said first detector and said second detector, each includes a chamber, partly formed by the detection surface and the optically transparent area, to provide for the emanating metabolite to be collected in and contacting the detection surface.

15. The device according to claim 14, wherein the optically transparent area of each chamber of the first detector and the second detector are configured for inspection of said detection surface.

16. The device according to claim 1, wherein the attachment portion is two attachment portions merged together.

17. A method of detecting changes in skin tissue comprising:
    attaching an attachment portion, comprising at least one first detector and at least one second detector at a defined distance from each other, wherein the first detector and the second detector are identical types of detectors; and wherein said second detector is a reference detector;
    detecting changes in dermis or epidermis by detecting a difference in detector responses between said first detector and said second detector; and wherein said first detector and said second detector are in fluid communication with said skin tissue and comprising a material configured to provide a measurable change in at least one of an electrical, a visual, and an optical property based on differences between the first detector and the second detector by an emanating metabolite from changes in dermis or epidermis.

18. The method according to claim 17, wherein the detection of changes is by chemical detection, and wherein said chemical detection of said first detector and of said second detector is by detection of changes in electrical or optical properties, or by detection of changes in chemical adsorption; or a combination thereof.

19. The device according to claim 1, wherein the detection of said chemicals indicates a change in dermis or epidermis.

\* \* \* \* \*